United States Patent
Sonnenschein et al.

(10) Patent No.: US 7,753,249 B2
(45) Date of Patent: Jul. 13, 2010

(54) STAPLING DEVICE

(75) Inventors: Minelu Sonnenschein, Meitar (IL);
Elazar Sonnenschein, Beer Sheva (IL);
Amir Govrin, Tel Aviv (IL)

(73) Assignee: Medigus Ltd., Omer (IL)

(*) Notice: Subject to any disclaimer, the term of this patent is extended or adjusted under 35 U.S.C. 154(b) by 124 days.

(21) Appl. No.: 10/526,845

(22) PCT Filed: Feb. 15, 2005

(86) PCT No.: PCT/IL2005/000194
§ 371 (c)(1),
(2), (4) Date: Apr. 27, 2007

(87) PCT Pub. No.: WO2005/115255
PCT Pub. Date: Dec. 8, 2005

(65) Prior Publication Data
US 2008/0000941 A1    Jan. 3, 2008

(30) Foreign Application Priority Data
May 27, 2004 (IL) .................................. 162187

(51) Int. Cl.
*A61B 17/072* (2006.01)
(52) U.S. Cl. .................... 227/176.1; 227/175.1; 227/19
(58) Field of Classification Search ... 227/175.1–182.1, 227/19; 606/153, 219
See application file for complete search history.

(56) References Cited

U.S. PATENT DOCUMENTS

| | | | | |
|---|---|---|---|---|
| 2,541,246 A | * | 2/1951 | Held | 606/205 |
| 3,554,520 A | * | 1/1971 | Grosko | 266/208 |
| 4,318,548 A | * | 3/1982 | Oberle et al. | 277/608 |
| 4,784,137 A | * | 11/1988 | Kulik et al. | 227/177.1 |
| 5,071,430 A | * | 12/1991 | de Salis et al. | 606/219 |
| 5,170,925 A | * | 12/1992 | Madden et al. | 227/175.1 |
| 5,653,373 A | * | 8/1997 | Green et al. | 227/175.1 |
| 5,897,562 A | * | 4/1999 | Bolanos et al. | 606/139 |
| 6,159,146 A | * | 12/2000 | El Gazayerli | 600/106 |
| 6,312,437 B1 | * | 11/2001 | Kortenbach | 606/139 |
| 6,835,200 B2 | * | 12/2004 | Laufer et al. | 606/153 |
| 6,872,214 B2 | * | 3/2005 | Sonnenschein et al. | 606/153 |
| 7,083,630 B2 | * | 8/2006 | DeVries et al. | 606/153 |
| 2001/0056282 A1 | * | 12/2001 | Sonnenschein et al. | 606/139 |
| 2004/0004105 A1 | * | 1/2004 | Jankowski | 227/176.1 |

\* cited by examiner

*Primary Examiner*—Rinaldi I. Rada
*Assistant Examiner*—Lindsay Low
(74) *Attorney, Agent, or Firm*—Roach Brown McCarthy & Gruber, P.C.; Kevin D. McCarthy (57) ABSTRACT

The invention is a stapling device comprised of an articulation section having a staple cartridge containing staples and parts of a staple-firing mechanism located at one end and an anvil portion located at the other end. The front surfaces of the anvil and the cartridge are curved. When the articulation section is bent the curved front surfaces of the anvil and the cartridge are brought opposite each other. As the distance between said curved surfaces is reduced, their curvature helps to correct transverse misalignment and to bring the anvil and the cartridge into the correct working relationship.

6 Claims, 11 Drawing Sheets

STAPLING DEVICE

FIELD OF THE INVENTION

The present invention relates to stapling devices. Specifically the invention relates to a stapling device comprised of a stapler cartridge comprising a supply of staples and parts of a staple firing mechanism, which is attached to one end of an articulation section, and an anvil portion, which is attached to the other end of the articulation section.

BACKGROUND OF THE INVENTION

In recent years, surgeons have been increasingly using surgical staples instead of sutures. Surgical staples and surgical stapling instruments have made many difficult procedures much simpler to perform, and significantly reduced the time required to perform them, thus allowing the patient to spend less time under general anesthesia.

In general, modern surgical stapling instruments for use on internal organs and tissues are comprised of a head containing a cartridge which holds the staples and a mechanism for ejecting the staples out of the cartridge, either sequentially or simultaneously, and driving them through the tissue. Typically, on the other side of the tissues to be stapled, there is an anvil, which deforms the staples into the shape required to hold the tissues together. The head and anvil together form the distal stapling portion of the instrument. There is a proximal portion which houses the actuator mechanism for firing the staples, and the mechanism for bringing the anvil and cartridge containing head to the desired distance and keeping them exactly aligned.

A basic consideration in the design of all staplers is the fact that it takes a substantial force to bend the staples. Consequently, at the time the staples are fired, the anvil and the head must be clamped rigidly together, or the force will cause them to separate, and the staples will not fully close. In addition, for the legs of the staples to curl to the shape required to hold the tissues together, the anvil and the staple dispensing part must be aligned precisely. Because of these limitations, in prior art staplers the stapler holding portion and the anvil portion of the device are either rigidly pivotally connected together or, for staplers having separate anvil and staple dispensing parts, the parts of the stapler are manually clamped together when they are at the desired location for stapling.

An improvement over the previously known prior art surgical staplers is disclosed in International Patent Application WO 02/39909 by the same applicant, the description of which, including references cited therein, is incorporated herein by reference. In WO 02/39909 is described a surgical stapler having a totally flexible connection between the anvil and staple dispensing portions of the instrument. In laparoscopic or open operations, such a totally flexible connection will allow stapling in hard-to-reach places. Moreover, such a totally flexible stapling instrument could be combined with a flexible endoscope, which will permit the instrument to be passed through natural orifices, such as the mouth, anus, or vagina. Any number of procedures could then be performed without the need to fully anesthetize the patient, and without opening the abdomen or other organs. A non-exhaustive list includes: removal of broad-based colonic polyps and small cancers; endoscopic treatment of gastroesophageal reflux disease (GERD), and full thickness biopsies of gastric lesions. All of which are typically performed under the influence of a general anesthetic.

The invention described in WO 02/39909 is directed towards providing a stapling device for a surgical endoscopic device provided with at least one flexible portion. The stapling device comprises two portions, a cartridge containing a supply of staples and a staple-firing mechanism and an anvil. One of the cartridge portions and one of the anvil portions is located, longitudinally displaced from one another along the longitudinal axis of said endoscopic device, with at least a part of said flexible portion between them.

According to the preferred embodiment of the invention, the flexible section comprises a two-way articulation section, the staple cartridge is located proximately to the proximal end of the articulation section and the anvil is located on the distal tip of the articulation section, and completely bending the articulation section using a fixed radius of curvature brings the two portions of the stapler into alignment.

To hold the two parts of the stapler together during firing, two locking pins or, preferably, screws that are stored in the anvil portion are extended and engage and lock into receptacles on the cartridge.

An ultrasound positioning assembly comprising two separate elements, one of which is located near the cartridge and the other near the anvil, is provided to verify that the parts of the stapling device are correctly positioned relative to each other prior to extending the screws and that there is the correct distance between them before firing the staples. Details of the design and operation of preferred embodiments of the ultrasound positioning system are disclosed in International Patent Application WO 02/068988 by the same applicant, the description of which, including references cited therein, is incorporated herein by reference.

The staple cartridge contains one or a plurality of arrays of staples. Each array consists of one or a plurality of staples. The firing mechanism for firing the arrays of staples comprises staple pushers actuated by cams that are actuated by proximal means. If the cartridge contains more than one array of staples, then an arrangement actuated from the proximal end of the endoscope is provided to index the cartridge after the firing of each of the arrays of staples.

As described in WO 02/39909 and summarized hereinabove, the alignment of the staple cartridge with the anvil is dependent on the design of the articulation section, which has to be capable of bring the two parts of the stapler into exact alignment when it is bent through an angle of 270 degrees. Only if the positioning system verified that the exact alignment had in fact been achieved could the alignment pins or screws be deployed locking the cartridge and anvil together so that the staples could be fired. The alignment accuracy required is about ±1.5 mm. If the articulation section is not able to achieve this degree of accuracy, then when the pins or screws are extended from the anvil they will not enter the matching receptacles in the anvil.

The require degree of accuracy is achievable if expensive manufacturing techniques are used for the production of the individual vertebrae and great care is taken in assembling the entire articulation section. However it has been found by the inventors of the current invention, that even with the most accurate articulation section, difficulties arise in aligning the parts of the stapler. There are two main reasons for these difficulties: firstly, as a result of repeated bending and unbending of the articulation section, wear of the parts takes place resulting in the creation of play between the vertebrae; secondly, when using the device within a body, foreign objects can enter the spaces between the vertebrae, preventing the complete bending of the articulation section.

It is a purpose of the present invention to provide a stapler device comprising a cartridge and an anvil located respectively on the proximal and distal ends of an articulation section in which the shape of the cartridge and the anvil assist in bringing the parts of the stapler into alignment for firing the staples, thus overcoming the difficulties of the prior art.

Further purposes and advantages of this invention will appear as the description proceeds.

SUMMARY OF THE INVENTION

In a first aspect the present invention is directed towards providing a stapling device comprised of an articulation section, a staple cartridge containing staples and parts of a staple-firing mechanism, and an anvil portion. The cartridge is located at one end of the articulation section and the anvil portion is located at the other end. The front surfaces of the anvil and the cartridge are curved. When the articulation section is bent, bringing the curved front surfaces of said anvil and the cartridge opposite each other, the curved surfaces help to correct transverse misalignment and to bring the anvil and the cartridge into the correct working relationship.

In a preferred embodiment, the cartridge is located at the proximal end of the articulation section and the anvil is located at the distal end.

In all embodiments the staple firing system of the stapler of the invention is arranged such that pulling the firing cams in a longitudinal direction causes the staples to exit the cartridge in a direction at right angles to the direction of motion of the cams.

The face of the cartridge is comprised of a curved surface having a curvature that must match the curvature of the front face of the anvil. The face of the cartridge can be comprised of a single curved surface. In a preferred embodiment, the center of curvature of the cartridge face in the area of the array is lowered relative to the center of curvature of the rest of the surface. This results in a cartridge having a surface comprised of two levels. The presence of the two levels assists in correcting longitudinal misalignment.

In a preferred embodiment the staple cartridge comprises a step structure in its curved face. The step structure is a reflector of ultrasound radiation and comprises one element of an ultrasound positioning assembly.

If a two-way articulation section is used, then the preferred shape of the surface of the cartridge is a section of a cylinder cut by a plane parallel to another plane containing the cylinder's longitudinal axis. For a four-way articulation section a spherical shape is preferred for the surface of the cartridge.

In another aspect the invention is directed to providing a method of bringing the anvil and cartridge of the stapling device of the invention into correct working relationship. The method comprises over-bending the articulation section causing the face of the anvil to be guided by the shape and design of the surfaces over the face of the cartridge into the correct working relationship.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

Figure 1:
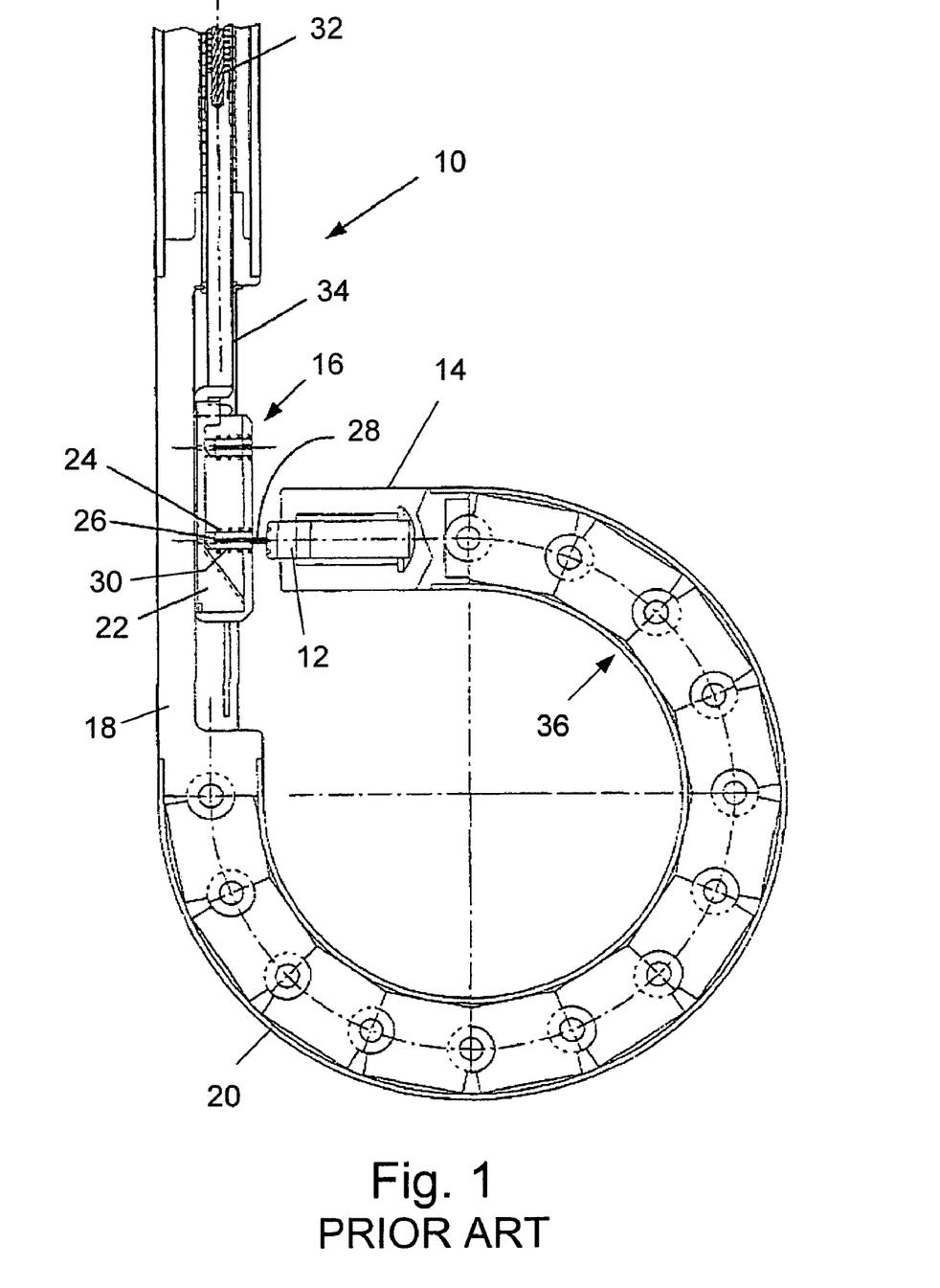
FIG. 1 is a schematic cross-sectional view showing the fixed portion and the articulation section of an endoscope, comprising a prior art stapler consisting of an anvil and a staple cartridge.

FIG. 1 is a schematic cross-sectional view of the distal section of an endoscope 10 comprising the stapler device disclosed in the above referenced WO 02/39909. In the figure is shown the anvil section 12, located in the distal tip 14 of the endoscope and the stapler cartridge 16, located in rigid section 18. Between distal tip 14 and rigid section 18 is located the articulation section 20. Parts of the stapler cartridge shown in FIG. 1 and described in WO 02/39909 are: one of the firing cams 22, a staple 24, and the corresponding staple pusher 26. One of the screws 28 is shown screwed out of its storage space in anvil 12 and into a receptacle 30 in cartridge 16 in order to enable the stapling to be carried out. Numeral 32 designates the firing cable that is attached to plunger 34 that is in turn connected to the cams in the staple cartridge.

As described in WO 02/39909 with reference to the GERD procedure, the endoscope is inserted into the patient's stomach through the esophagus with the articulation section straight and, when it has been inserted the proper depth, the articulation section is then bent to carry out the fundoplacation. The correct functioning of the device depends on the articulation section performing precisely as designed to bring the two parts of the stapler into the correct working relationship. The term "correct working relationship" is understood herein to mean that the anvil is brought into the exact position opposite the cartridge that will allow the locking screws to be extended as shown in FIG. 1. This term also implies that the correct distance is reached between the faces of the anvil and the cartridge. Thus, when the correct working relationship is achieved, the legs of the staples will enter the depressions provided on the face of the anvil and will be properly curled to hold the tissue being stapled.

As a result of "wear and tear" of the parts that make up the vertebra section, dirt or any foreign matter enters the spaces (indicated by arrow 36 in FIG. 1) between some or all of the vertebrae, and the fact that it is not possible to achieve the design goal of zero freedom of motion of the vertebrae, especially in the transverse direction, unwanted freedom of motion, or "play" often is discovered while working with the prior art staplers. The result of play of this type is that upon activation of the articulation cable until the articulation section is through the designed 270 degrees, the anvil will not be in the correct position facing the cartridge. The problem of misalignment can be broken up into two components—one component in the direction of the longitudinal axis of the articulation section and the other component in the transverse direction. If the problem is misalignment in the longitudinal direction, then it can be overcome by continued pulling on the articulation cable, bending the articulation section slightly more than 270 degrees and using the ultrasound positioning system to verify when the correct working relationship is received.

Misalignment in the transverse direction cannot be corrected by further bending of the articulation section. If the problem is discovered during routine testing then the vertebrae section must be taken apart and thoroughly, cleaned and inspected with damaged parts being replaced. This is a very time consuming and expensive procedure and all the more so because of the large number of cables, wires, fiber optics, irrigation channels, etc. that pass through channels in the vertebrae from the proximal end of the endoscope to the distal tip. If the problem is discovered after the procedure has begun, then the surgeon has two options. He can straighten the articulation section and rebend it repeatedly until, by "chance", the desired alignment is achieved or, if this fails, he can withdraw the endoscope and begin again with a different instrument if one is available.

The solution to the problem of incorrect alignment of the anvil and cartridge caused by inaccuracy in the bending of the articulation section provided by the present invention is to give the cartridge and anvil matching curved surfaces which will interact to force the distal tip of the endoscope towards proper alignment as the articulation cables are pulled causing the front face of the anvil to approach the face of the cartridge.

Figure 2:
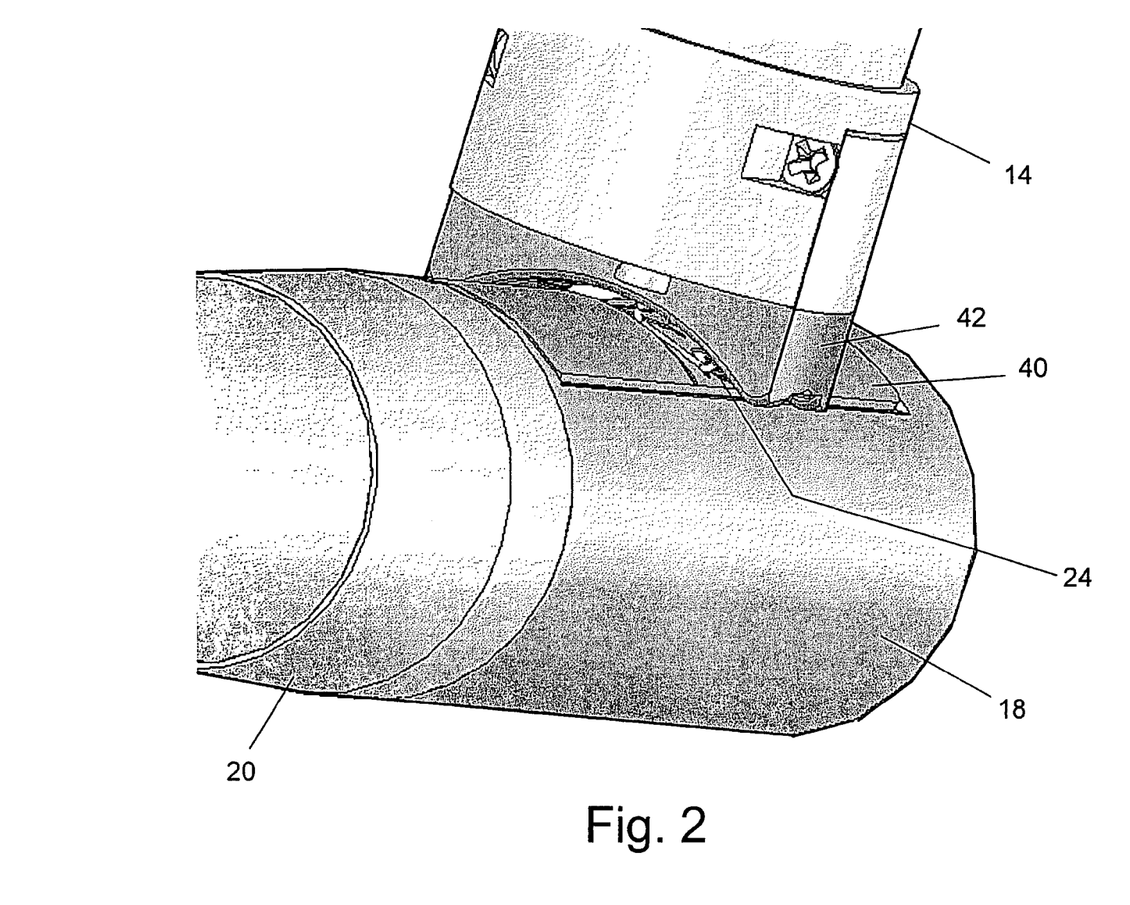
FIG. 2 shows the anvil and the cartridge of the invention in the aligned position during firing of the staples.

FIG. 2 shows the anvil unit 42 and the cartridge 40 of the invention in the correct working relationship during firing of the staples. Replaceable cartridge 40 is shown in the receptacle in the rigid section 18 of the endoscope provided for this purpose between the flexible section of the insertion tube (not shown in the figure) and the articulation section 20. Replaceable anvil unit 42 is in the receptacle provided in distal tip 14 of the endoscope, located at the distal end of articulation section 20. For illustrative purposes, one of the staples 24 that has been ejected from the cartridge and whose legs have been curled against the face of the anvil is shown in the figure.

Figure 3:
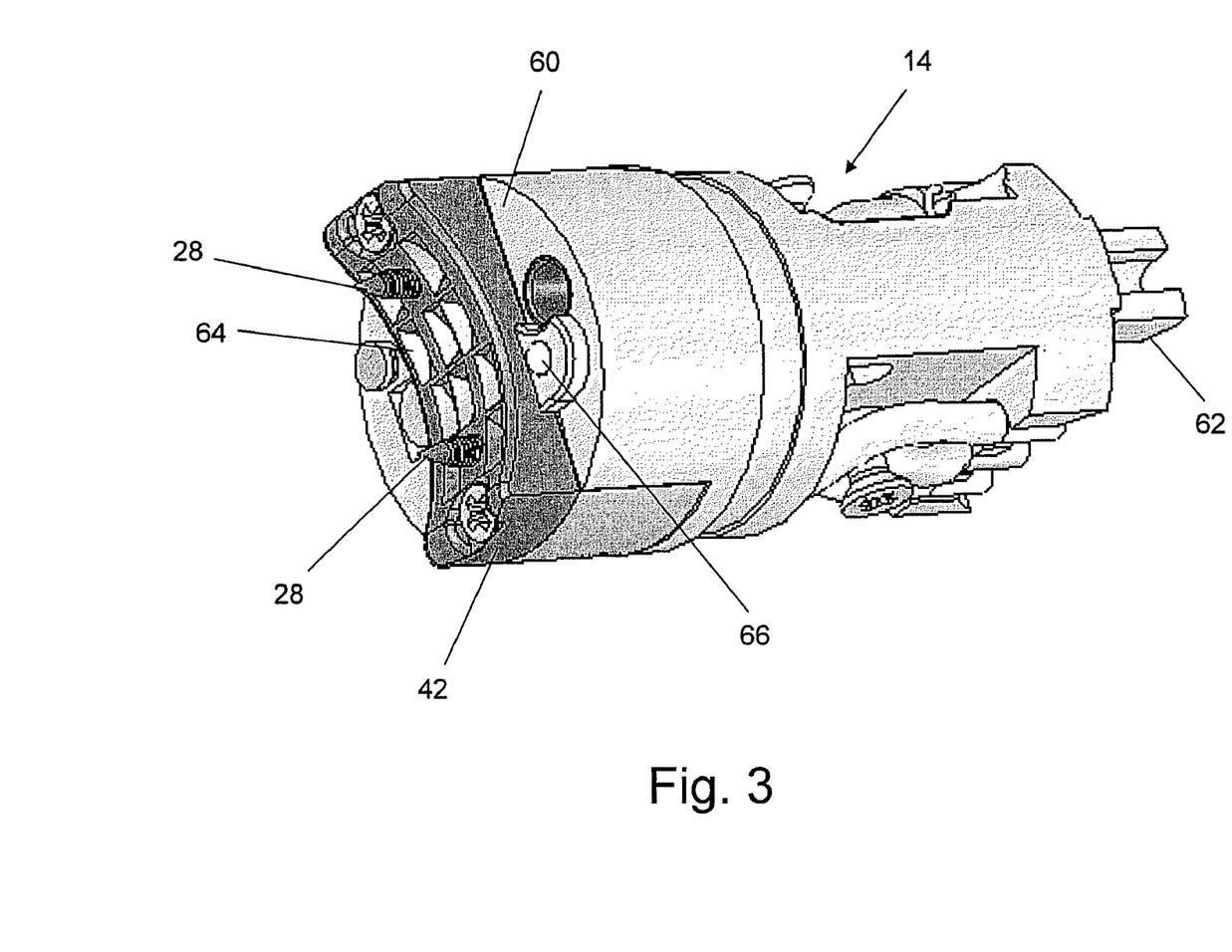
FIG. 3 is a perspective view showing the anvil unit of the invention mounted in the distal tip.

FIG. 3 is a perspective view showing a preferred embodiment of the anvil unit 42 of the invention. The anvil unit 42 fits into the socket on distal tip 14 in such a way that it projects beyond the distal face 60 of distal tip 14. Shown on the curved face of the anvil unit 42 are the depressions 64 in which the legs of the staples are curled. The two locking screws 28 are shown partially extended. The cover plates on the proximal part of the distal tip 14 have been removed revealing some of the channels leading to the endoscope devices and accessories located on distal face 60 and to the interface 62 with the most distal vertebra of the articulation section. With the exception of ultrasound transducer 66, none of these elements or the mechanism for advancing and withdrawing screws 28, some of which is contained in distal tip 14 and some of which is contained in anvil unit 42, are relevant to the present invention and therefore will not be described herein.

According to the invention, the face of the cartridge is comprised of a smooth curved surface having a curvature that matches the curvature of the front face of the anvil.

Figure 4:
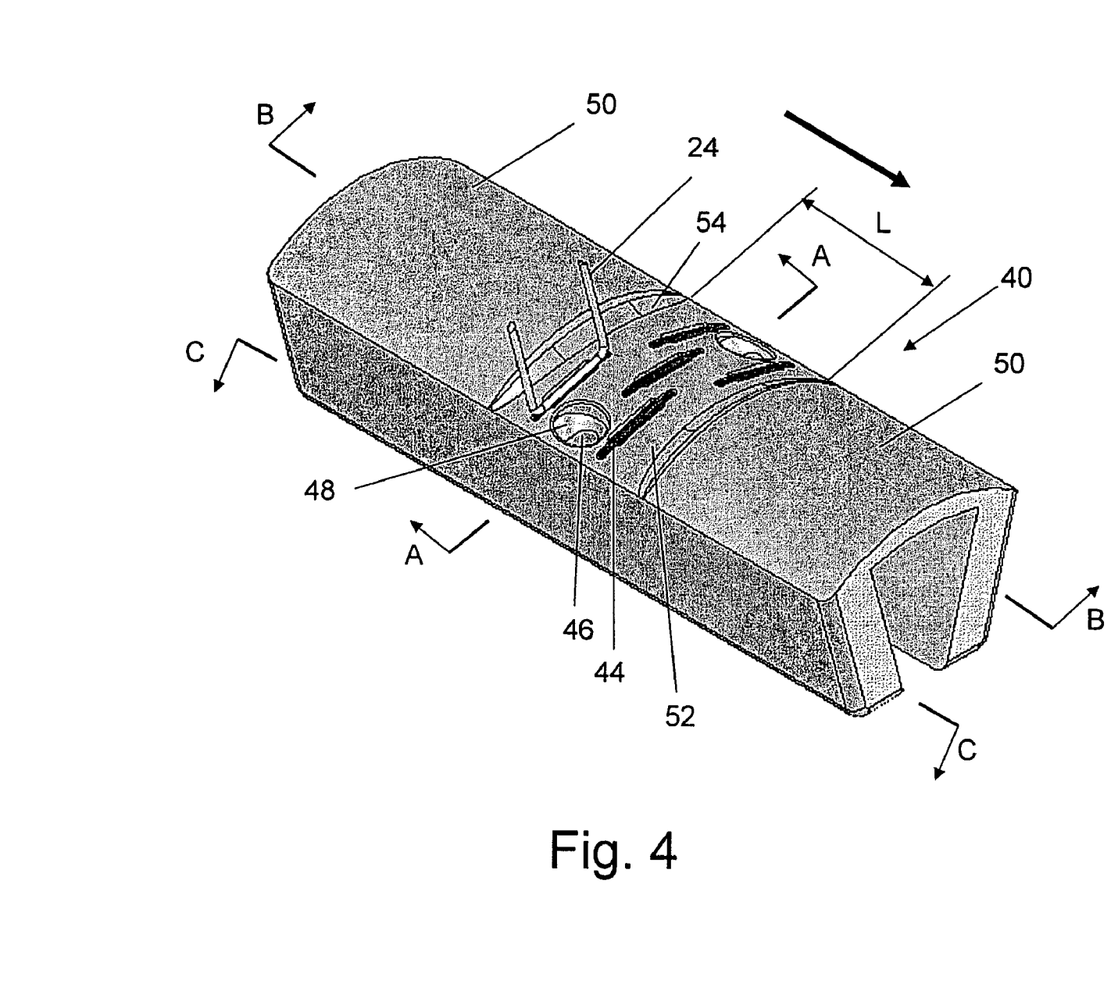
FIG. 4 is a perspective view showing the cartridge of the invention.

FIG. 4 is a perspective view showing a preferred embodiment of the cartridge 40 of the invention. The bold arrow in the figure (as well as in FIGS. 5 to 8) indicates the distal direction. For purposes of illustrating the invention, a cartridge from which one array comprising five staples is ejected is described herein. It will, however, be understood by skilled persons that arrays having a different number of staples, cartridges having more than one array, and, if more than one array is present, indexing means can be provided within the framework of the present invention for example by making use mutatis mutandis of the teachings of WO 02/39909.

The parts of the firing mechanism that are located within the cartridge and the interaction between them for firing the staples are similar to those described in WO 02/39909 and the description in this publication applies mutandis mutatis to the present invention as well. The major difference between the prior art cartridge and that of the present invention is the curved surface of the face of the cartridge of the invention. In order for the staples to be ejected from the cartridge perpendicular to the curved surface, the stored staples, the cams, etc. of the firing mechanism must be arranged at angles to each other and not in parallel planes as in the prior art. Because of the limitations on the diameter of the endoscope, the arc length of the curved surface of the cartridge is not large enough to allow the storage of two staples side-by-side at the correct angle. Changing the configuration of the array such that the staples are separated from each other in the longitudinal direction can solve this problem. Choosing this solution however will lead to the undesirable result of requiring a longer cartridge and, therefore a longer rigid section for the endoscope.

The solution chosen for the preferred embodiment of the invention is to lower the center of curvature of the cartridge face in the area of the array relative to the center of curvature of the rest of the surface. This solution results in the two-level design shown in the figures and described hereinbelow. The two-level design not only allows for efficient storage and firing of the staples but also simplifies the process of bringing the two parts of the stapler into correct working relationship as will be described hereinbelow.

Referring to the figures, it can be seen that the curved surface of the cartridge 40 that faces the anvil 42 comprises two levels. Upper level 50 comprises two sections that are located at the proximal and distal ends of cartridge 40 and lower level 52 is located in the center of the cartridge above the array of staples. The lower level 52 has a length L a little longer than the width of the anvil face (see FIG. 3) in order to accommodate the layers of tissue that are compressed between them. Shown in lower level 52 are the slots 44 through which the staples 24 of the array are ejected and the two bores 46 with their beveled entrances 48 into which the locking screws enter. The interfaces between the two sections of upper level 50 and lower level 52 are the two sloping walls 54.

Figure 5:
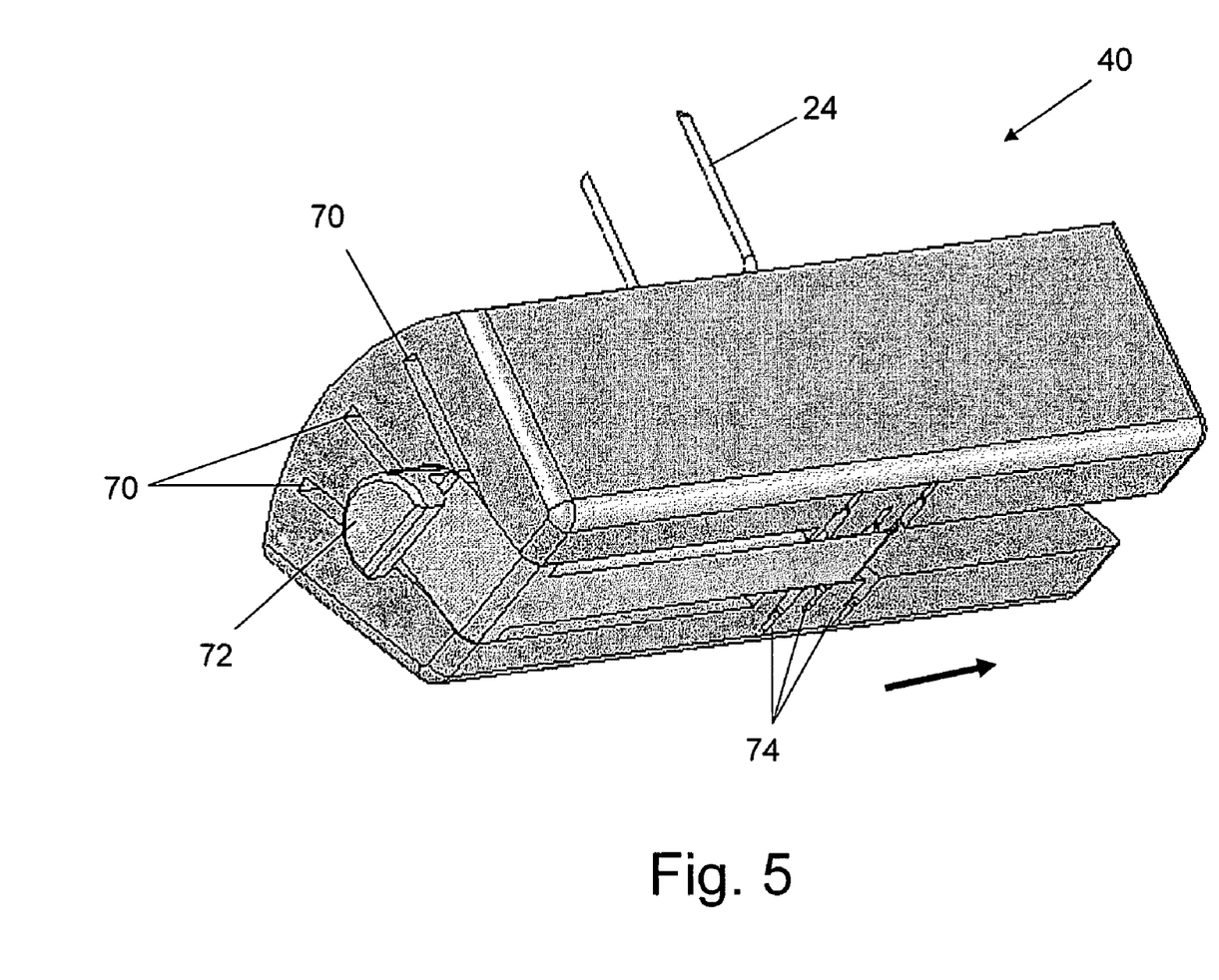
FIG. 5 is a bottom view of stapler cartridge of the invention.

FIG. 5 is a bottom view of stapler cartridge 40 of the invention. The cams fit into slots 70, 72 is the cross member to which all of the cams are attached and which is in turn connected to the plunger 34 (see FIG. 1), numeral 74 designates the slots into which the staple pushers fit, and 24 designates a staple. It is to be noted that the cams are aligned in a direction parallel to the longitudinal axis of the cartridge and the staple pushers and the staples are stored in the cartridge at right angles to the cams. As a result of this arrangement, the staples exit the cartridge in a direction transverse to the longitudinal motion of the cams caused by pulling on the plunger.

Figure 6:
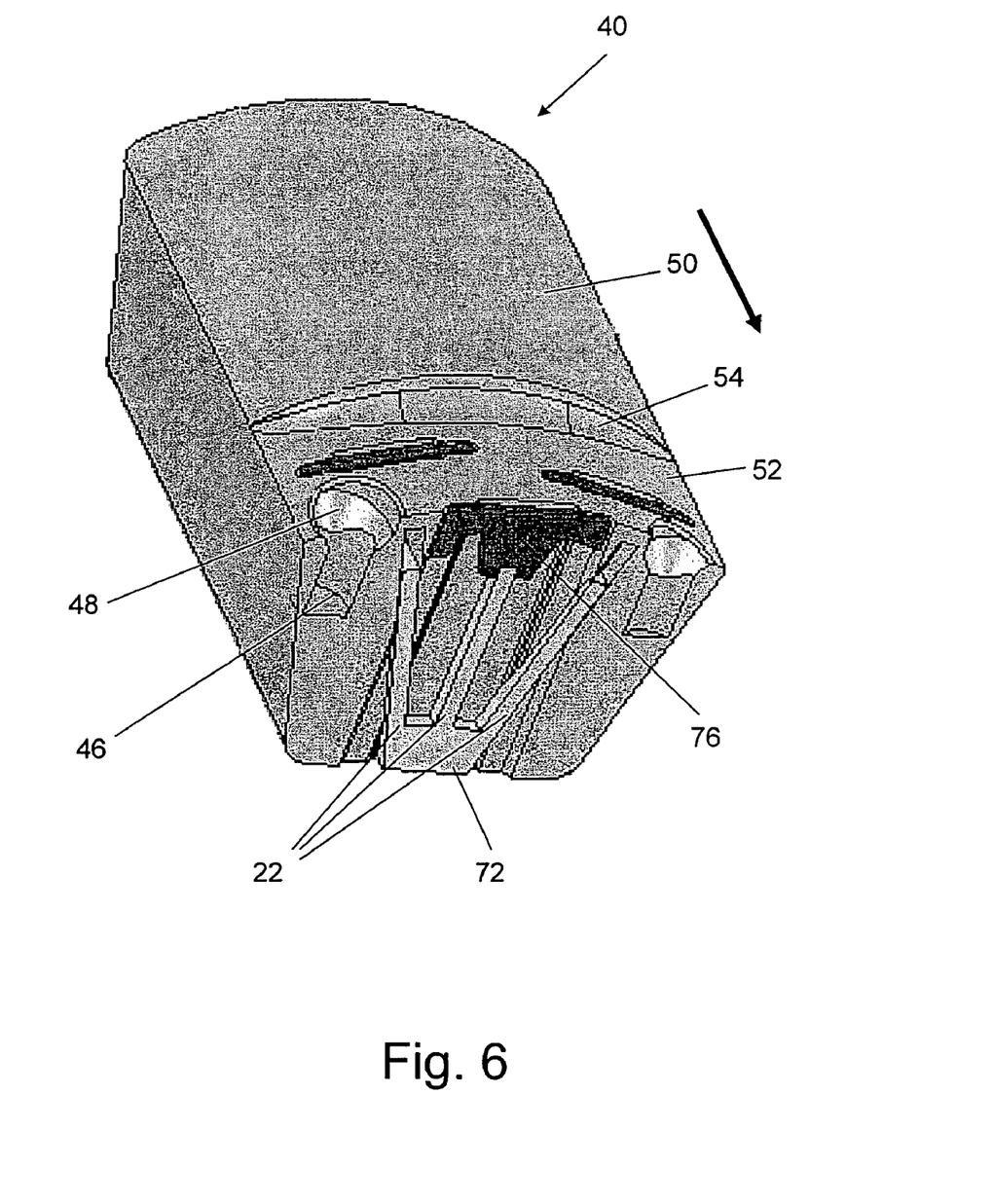
FIGS. 6, 7, and 8 are sectional views along planes A-A, B-B, and C-C in FIG. 4 respectively.
Figure 7:
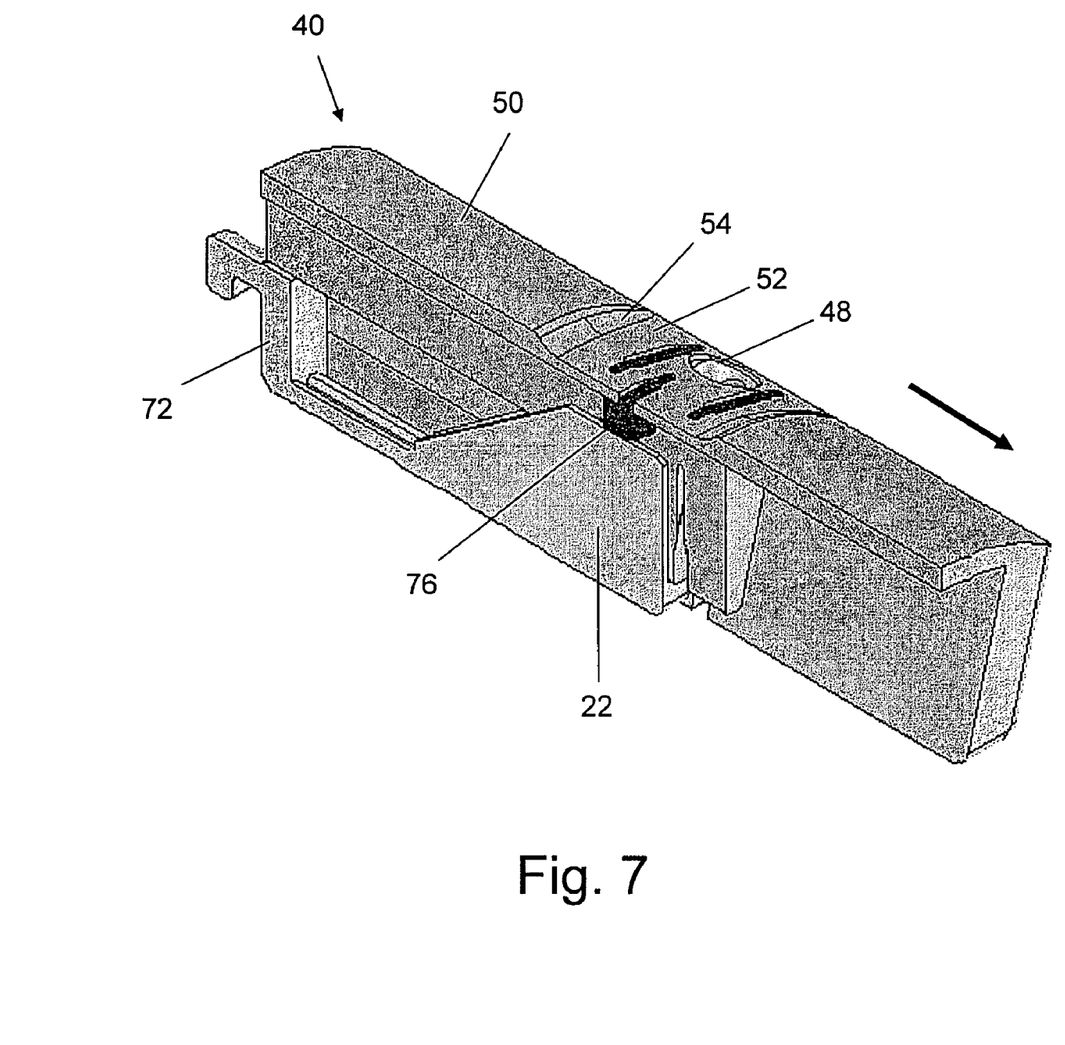
Figure 8:
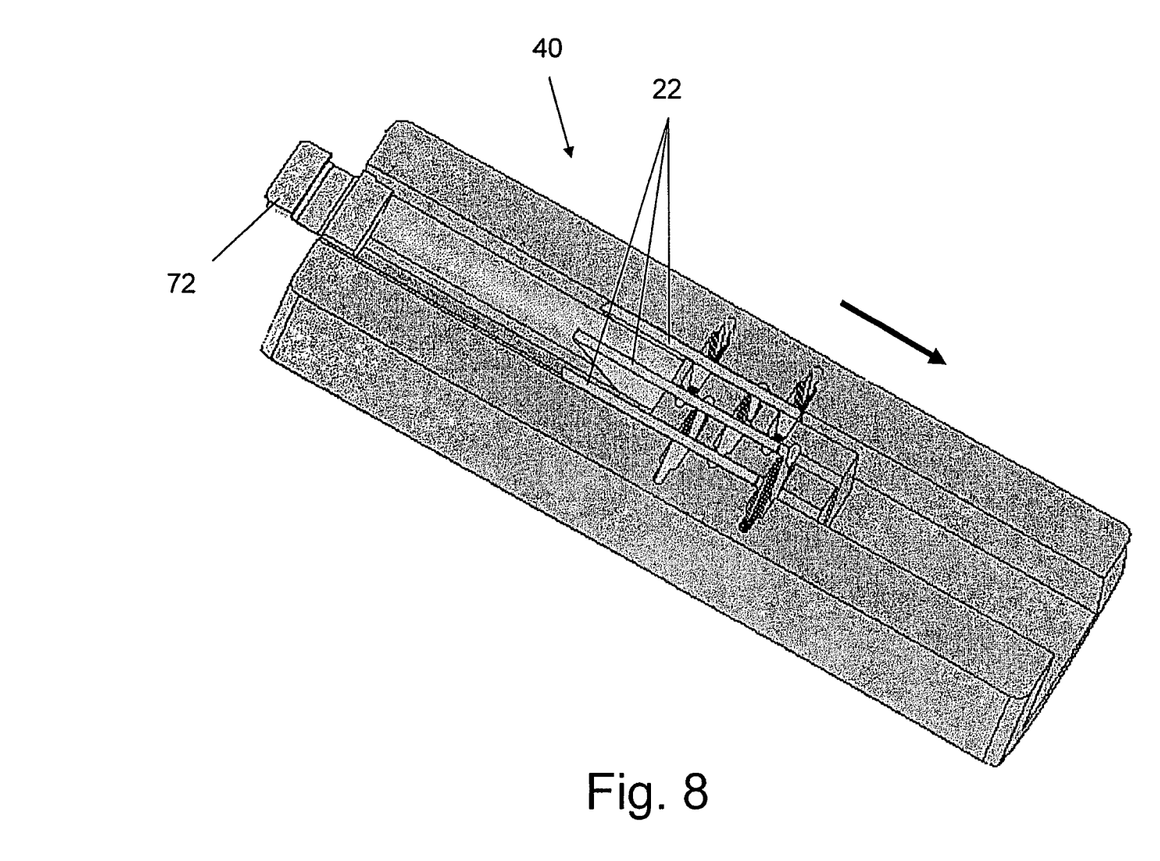

FIGS. 6, 7, and 8 are sectional views along planes A-A, B-B, and C-C in FIG. 4 respectively. Shown in these figures are the cams 22, cross member 72, and staple pushers 76. The staples have been omitted for clarity. In FIG. 6 is shown clearly the two levels 50 and 52 of the surface of the cartridge 40 and the inclined wall 54 that connects them. Also seen in this figure is the beveled entrance 48 to the bores 46 into which the locking screws are threaded. The slope of the beveled entrance helps to make the final adjustment of the alignment between the parts of the stapler, since the advancing screws will move down the slope into the bore, pulling the anvil into the precise position relative to the array of staples that is required for firing.

Figure 9:
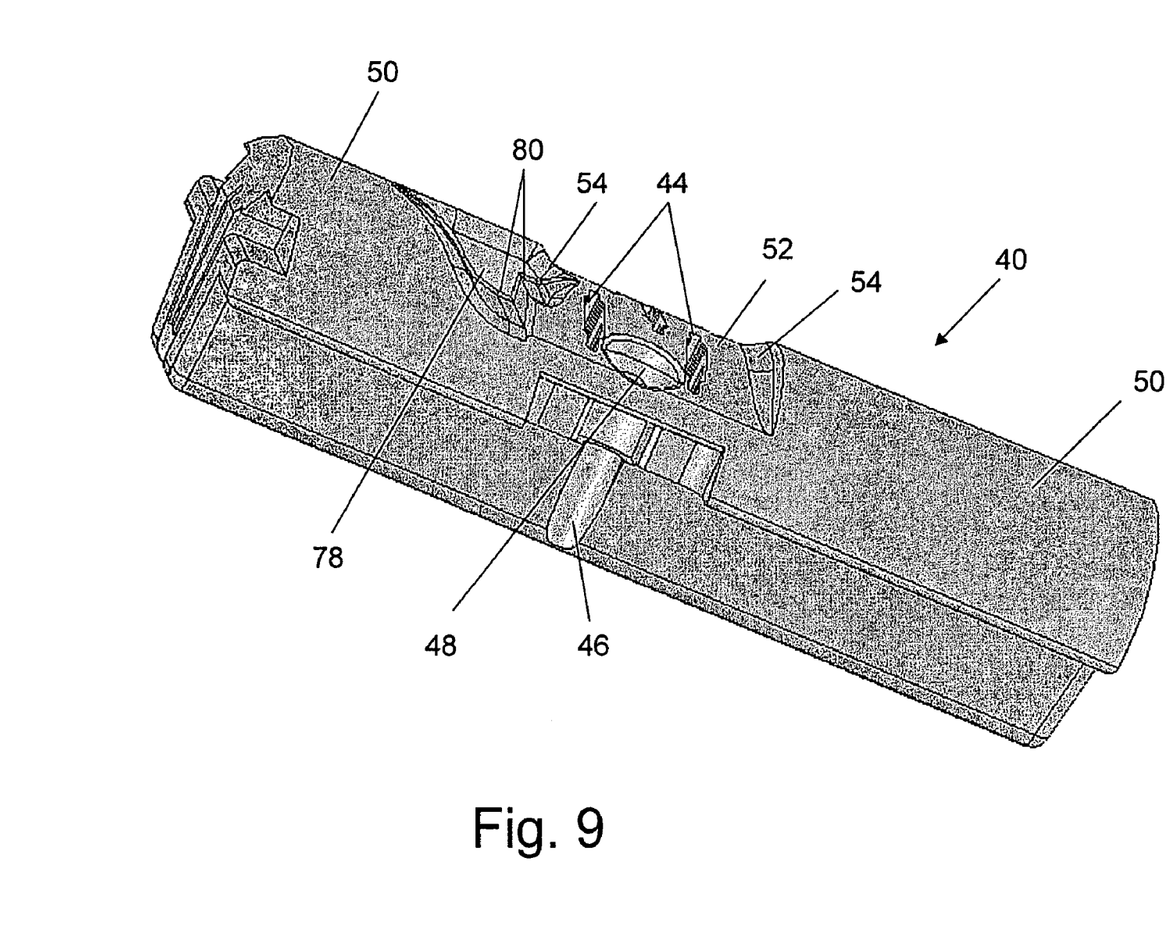
FIG. 9 and FIG. 10 are perspective views of an embodiment of the cartridge of the invention comprising the reflector component of the ultrasound positioning assembly.
Figure 10:
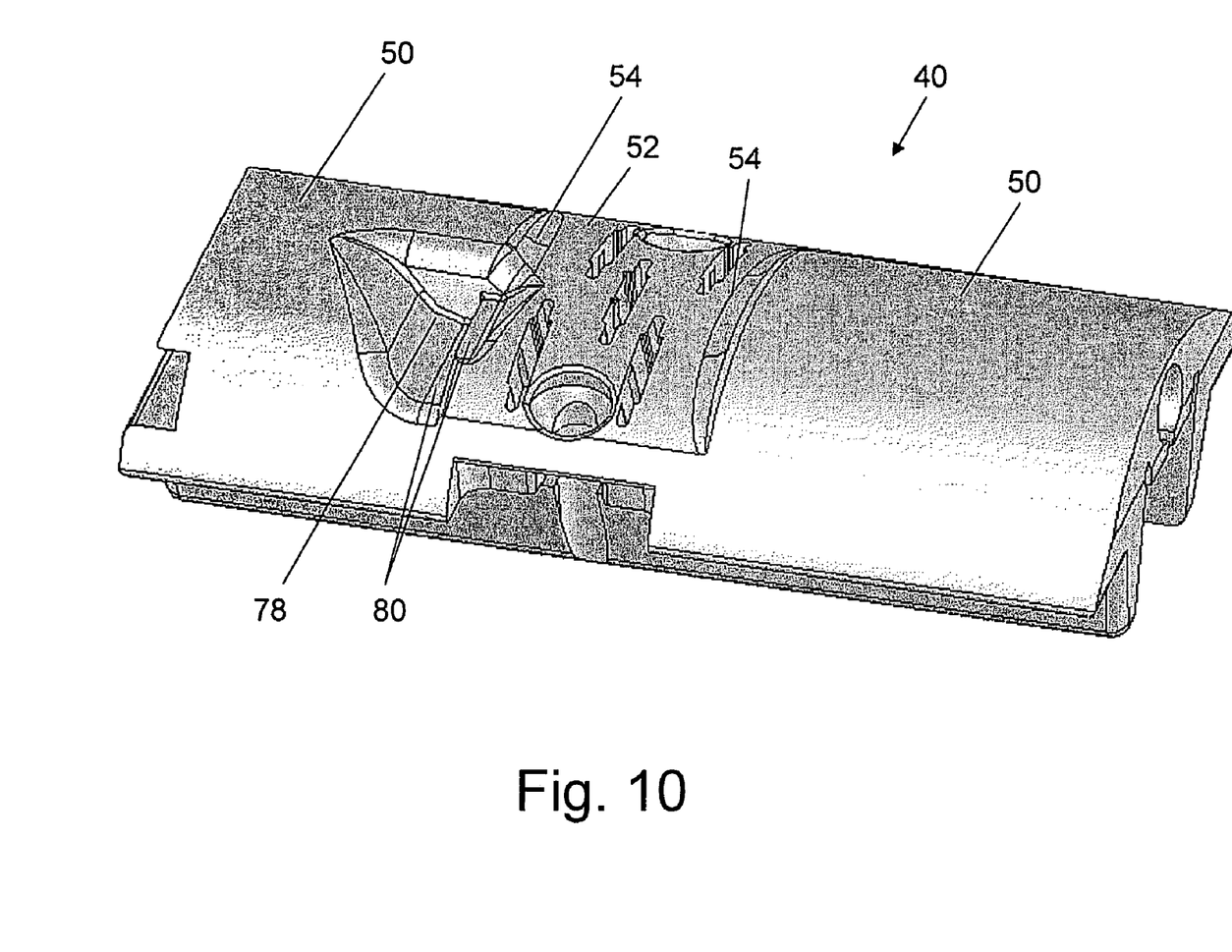

FIG. 9 and FIG. 10 are perspective views of an embodiment of the cartridge of the invention comprising the reflector component of the ultrasound positioning assembly. A portion of the proximal section of upper level 50 is removed to form recess 78. Two parallel horizontal planar "steps" 80 are created in recess 78. Steps 80 are reflectors that are used to make the ultrasound measurements as described in the above referenced International Patent Application WO 02/068988. It is to be noted that except for the step 80, all the edges of the anvil and cartridge, and especially those of recess 78, are "rounded" to minimize injury to the tissue that is clamped between the cartridge and the anvil.

Figure 11:
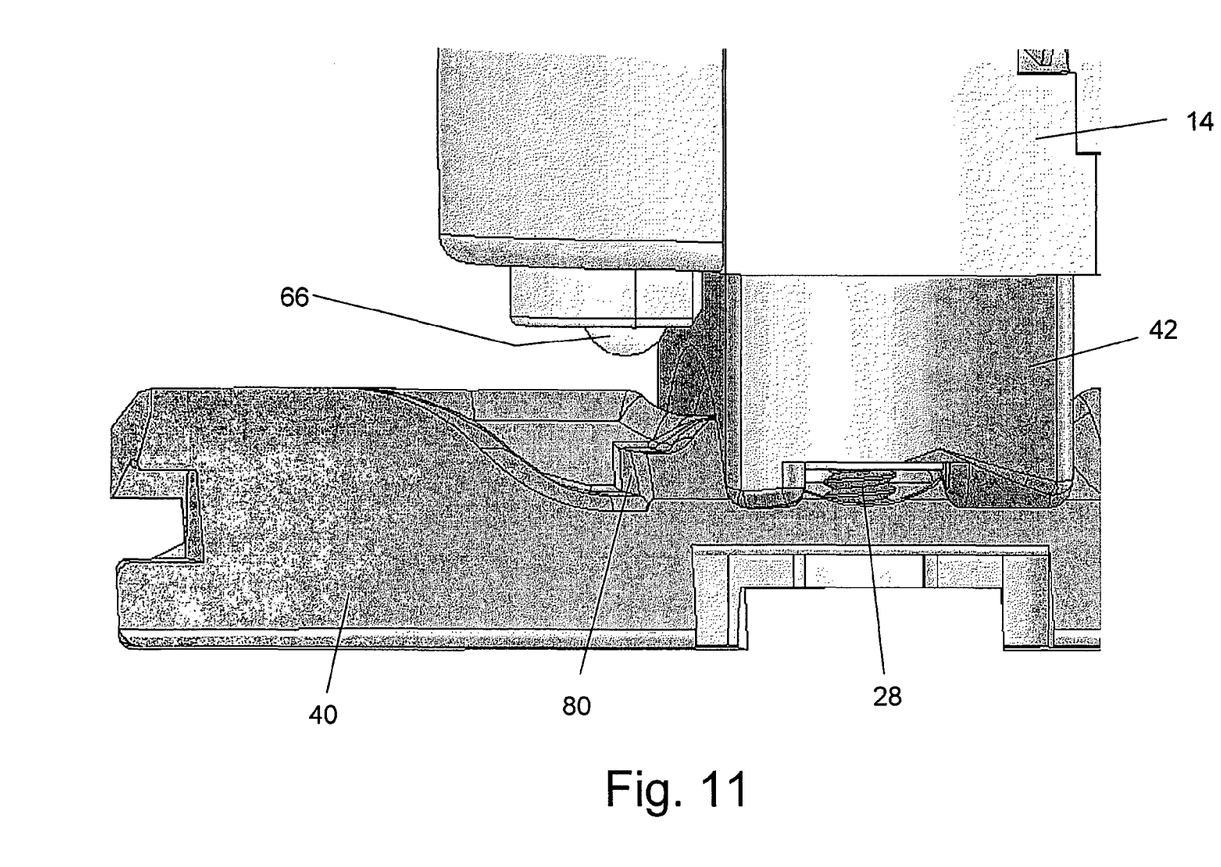
FIG. 11 shows the alignment of the ultrasound transducer and reflector when the stapler is ready for firing.

FIG. 11 shows the alignment of the ultrasound transducer 66 and reflector 80 when the stapler is ready for firing. The tissue to be stapled is not shown to allow a clear view showing the relative alignment of the anvil 42 and cartridge 40.

Both the anvil and the cartridge can be made for one-time use, after which they are discarded, or for multiple uses, in which case the cartridge must be reloaded with a new array of staples after each use. They can be made of any suitable material known to the art such as stainless steel or plastic. For medical applications the material should be biocompatible, that is it should not cause any irritation to any tissue with which it comes into contact. The bores in the cartridge can be threaded to receive the locking screws or, in the case of plastic cartridges, the bores can be smooth to be used with self-tapping screws.

In principle, the surfaces of the anvil and the cartridge can be of any shape as long as they are matching. The preferred curvature for use with a two-way articulation section as described hereinabove, i.e. one that can bend and unbend in a single plane, is a section of a cylinder cut by a plane parallel to a plane containing its axis. For use with a four-way articulation section, i.e. one that can be bent and unbent in two mutually perpendicular planes, a spherical shape is preferred.

Referring to FIGS. 1 to 4, it can be seen how the design of the anvil and cartridge of the invention aid in proper alignment of the two elements of the stapler. Consider first misalignment in the direction transverse to the longitudinal axis of the cartridge. As the anvil approaches the cartridge, then, the curved front face of the anvil begins to press the intervening tissue against the front surface of the cartridge. Continued force exerted on the articulation cable will tend to force the anvil closer to the cartridge. As a result of this force, the curved face of the anvil will "feel the curvature" of the curved face of the cartridge through the tissue and anvil to "slide down" the cartridge face until alignment is achieved. The properties of the tissue assist this process by reducing the frictional force between the surfaces. The amount of transverse misalignment that can be corrected by this method is relatively large being essentially equal to half of the width of the cartridge on either side of the correct alignment position.

Along the direction of the longitudinal axis of the cartridge/articulation section, the inaccuracy in the bending sometimes results in the anvil "overshooting" the cartridge. As described hereinabove, with prior art staplers, this type of misalignment is corrected by exerting force on the articulation cable to cause the articulation section to continue bending and consequently the anvil will slide on the surface of the cartridge. The ultrasound positioning system is used to determine when the correct alignment has been achieved. This procedure is very difficult to carry out because it requires the physician to exert a great deal of force, not only to bend the articulation section but also to overcome the resistance of the layers of tissue pressed between the anvil and cartridge. Further he must constantly observe the ultrasound positioning system while making very precise movements, and usually very small adjustments to the force exerted, in order to guide the anvil into the correct working relationship with the cartridge. Finally he must hold the position and execute the procedure of advancing the locking screws and screwing them into the cartridge. In the case of the prior art stapler, if there existed any freedom of motion between any of the parts of the articulation section, then attempting to correct for longitudinal misalignment in the manner described, would invariably result in misalignment in the transverse direction and it would not be possible to bring the two parts of the stapler into correct working relationship.

The interdependence of the longitudinal and transverse alignment that exists for the prior art staplers does not exist with the stapler of the invention. Once the anvil is close enough to press the tissue over the surface of the cartridge, the transverse alignment is maintained by the curved surfaces of the cartridge and anvil, while the anvil slides back and forth longitudinally on the surface of the cartridge. In the case of the preferred embodiment shown in the figures, the two-level design assists in achieving longitudinal alignment since, as the articulation cable is pulled, the anvil will slide along upper level 50 until it reaches the sloping wall 54 and then "fall down" onto lower level 52 in correct alignment, with its face opposite the array of staples.

With the articulation section described in WO 02/39909, a bending force on the order of 15 to 20 Kg must be exerted on the articulation cables to fully bend the articulation section. The articulation section and cable are designed for a maximum bending force of approximately 50 Kg and the articulation section designed to allow it to be bent through an angle of greater than 270 degrees. The method of the present invention to correct both transverse and longitudinal misalignment is to bend the articulation section to approximately 270 degrees, bringing the distal tip close to the front of the cartridge and then exerting extra force, over-bending, i.e. bending beyond 270 degrees the articulation section, and thereby clamping the tissue and correcting misalignment as described hereinabove.

Although embodiments of the invention have been described by way of illustration, it will be understood that the invention may be carried out with many variations, modifications, and adaptations, without departing from its spirit or exceeding the scope of the claims.

The invention claimed is:

1. A stapling device comprised of an articulation section, a staple cartridge containing one or more arrays of staples and parts of a staple-firing mechanism, said cartridge having a facing surface comprising an area having slots through which the staples of said arrays are fired and two bores associated with each said arrays, and an anvil portion comprising two locking screws and a facing surface through which said locking screws can be extended, wherein said cartridge is located at either the proximal or the distal end of said articulation section and said anvil portion is located at the other end of said articulation section; characterized in that:
    (a) the facing surfaces of said anvil and said cartridge are curved surfaces having matching curvatures such that, when said articulation section is bent bringing said curved facing surfaces of said anvil and said cartridge close to each other, said curved surfaces slide over one another, thereby helping to correct transverse misalignment; and
    (b) the center of curvature of said facing surface of said cartridge in said area having said slots is lowered relative to the center of curvature of the rest of said facing surface, resulting in a surface having two levels, wherein an upper level comprises two sections that are located at the proximal and distal ends of said cartridge and a lower level is located in the center of said cartridge above said array of staples; said lower level has a length a little longer than the width of the face of said anvil; said two sections of said upper level are connected to said lower level by means of two sloping walls; characterized in that as said articulation section is bent bringing said curved facing surfaces of said anvil and said cartridge close to each other said curved facing surface of said anvil slides down said sloping walls until said curved facing surface of said anvil is positioned over said lower level in said curved facing surface of said cartridge, thereby assisting in correcting longitudinal-misalignment and bringing said locking screws in said anvil directly opposite said bores in said cartridge,
thereby allowing the parts of said stapling device to be brought into the correct working relationship.

2. A stapling device according to claim 1, wherein the cartridge is located at the proximal end of the articulation section and the anvil is located at the distal end of said articulation section.

3. A stapling device according to claim 1, further comprising a recess and step structure in the curved face of the staple cartridge, wherein said step structure is a reflector of ultrasound radiation that comprises one element of an ultrasound positioning assembly used to verify that the parts of said stapling device are in the correct working relationship.

4. A stapling device according to claim 1, wherein the articulation section is a two-way articulation section and the surface of the anvil is a section of a right circular cylinder cut by a plane parallel to its axis.

5. A method of bringing the anvil and cartridge of the stapling device of claim 1 into correct working relationship, said method comprising over-bending the articulation section.

6. A stapling device according to claim 1 and further comprising a plunger, wherein the parts of the staple-firing mechanism comprise cams and staple pushers; wherein pulling on said plunger causes said cams to move longitudinally in the cartridge, said longitudinal movement causing said staple pushers to rise towards the curved front surface of said cartridge and the staples to exit said cartridge in a direction at right angles to the direction of motion of said cams.

* * * * *